United States Patent
Chen (10) Patent No.: US 6,344,050 B1
(45) Date of Patent: Feb. 5, 2002

(54) USE OF PEGYLATED PHOTOSENSITIZER CONJUGATED WITH AN ANTIBODY FOR TREATING ABNORMAL TISSUE

(75) Inventor: James C. Chen, Bellevue, WA (US)

(73) Assignee: Light Sciences Corporation, Issaquah, WA (US)

( * ) Notice: Subject to any disclaimer, the term of this patent is extended or adjusted under 35 U.S.C. 154(b) by 0 days.

(21) Appl. No.: 09/218,336

(22) Filed: Dec. 21, 1998

(51) Int. Cl.[7] .................................................. A61N 7/00
(52) U.S. Cl. ............................ 607/88; 128/898; 606/2; 606/14
(58) Field of Search ............................... 606/2, 3, 7, 10, 606/11, 12, 14, 15; 424/78.08, 78.17; 128/898; 530/390.1, 391.7; 607/58

(56) References Cited

U.S. PATENT DOCUMENTS

| | | | |
|---|---|---|---|
| 5,109,016 A | | 4/1992 | Dixon et al. ................. 514/410 |
| 5,198,460 A | | 3/1993 | Pandey et al. .............. 514/410 |
| 5,219,564 A | * | 6/1993 | Zalipsky et al. .......... 424/78.17 |
| 5,308,604 A | | 5/1994 | Sinn et al. .................. 424/1.53 |
| 5,308,608 A | | 5/1994 | Dolphin et al. ................. 424/9 |
| 5,611,793 A | | 3/1997 | Wilson et al. .................. 606/2 |
| 5,728,090 A | * | 3/1998 | Martin et al. ................... 606/3 |

FOREIGN PATENT DOCUMENTS

| | | |
|---|---|---|
| WO | WO 91/10743 | 6/1993 |
| WO | WO 98/11827 | 3/1998 |
| WO | WO 98/50387 | 11/1998 |

OTHER PUBLICATIONS

Alleman, Eric; Brasseur, Nicole; Benerezzak, Ouhida; Rousseau, Jacques; Kudrevich, Svetlana V.; Boyle, Ross W.; Leroux, Jean–Christophe; Gurny, Robert; and Van Lier, Johan E. "PEG–coated Poly(lactic acid) Nanoparticles for the Delivery of Hexadecafluoro Zinc Phthalocyanine to EMT–6 Mouse Mammary Tumours." J. Pharm. Pharmacol. vol. 47. 1995. pp. 382–387.

Alleman, Eric; Rousseau, Jacques; Brasseur, Nicole; Kudrevich, Svetlana V.; Lewis, Karina; and Van Lier, Johan E. "Photodynamic Therapy Of Tumors With Hexadecafluoro Zinc Phthalocyanine Formulated In Peg–Coated Poly (Lactic Acid) Nanoparticles." Int. J. Cancer. vol. 66 1996. pp. 821–824.

(List continued on next page.)

Primary Examiner—Linda C. M. Dvorak
Assistant Examiner—R. Kearney
(74) Attorney, Agent, or Firm—Ronald M. Anderson (57) ABSTRACT

A photosensitizer suitable for use in administering photodynamic therapy (PDT), conjugated with antibodies that are targeted to antigens on abnormal tissue and polyethylene glycol (PEG) or other polymer that extends the residence time of the conjugate within a patient's body. The resulting pegylated targeted conjugate is administered to a patient, and after the antibodies have had sufficient time to bind with the antigens, light from an external or internal source having a waveband corresponding to an absorption waveband of the photosensitizer is administered. Use of an external light source that emits relatively long wavelength light enables the light to pass through any intervening dermal layer and normal tissue between the external light source and the treatment site. Since the photosensitizer in the conjugate is bound to the abnormal tissue, the light therapy has minimal effect on the intervening normal tissue. Furthermore, the efficacy of the PDT is enhanced due to the increased concentration of the photosensitizer of the conjugate linked to the abnormal tissue.

25 Claims, 3 Drawing Sheets-

OTHER PUBLICATIONS

Byers, V.S. and Baldwin, R.W. "Monoclonal Antibody Conjugates with Cytotoxic Agents for Cancer Therapy ." *New Directions in Cancer Treatment*. Ian Magrath (ed.). Springer–Verlag: New York, 1989. Ch. 17. pp. 325–341.

Cannizzaro, Scott M.; Padera, Robert F.; Langer, Robert; Rogers, Rick A.; Black, Fiona E.; Davies, Martyn C.; Tendler, Saul J.B.; and Shakesheff, Kevin M. "A Novel Biotinylated Degradable Polymer for Cell–Interactive Applications." Biotechnology and Bioengineering. vol. 58, No. 5, Jun. 5, 1998. pp. 529–535.

Coombes, A.G.A.; Tasker, S.; Lindblad, M.; Holmgren, J.; Hoste, K.; Toncheva, V.; Schacht, E.; Davies, M.C.; Illum, L; and Davis, S.S. "Biodegradable polymeric microparticles for drug delivery and vaccine formulation: the surface attachment of hydrophilic species using the concept of the poly(ethylene glycol) anchoring segments." Biomaterials. vol. 18, No. 17. 1997. pp. 1153–1161.

Fidias, Panos. "Monoclonal Anitbody Therapy for Solid Tumors: An Overview." *Monoclonal Antibody–Based Therapy of Cancer*. Michael L. Grossbard (ed.). Marcel Dekker, Inc.: New York, 1998. pp. 281–307.

Fritzberg, Alan R. "Biorecognition of Antibodies in vivo: Potential in Drug Targeting," Journal of Molecular Recognition, vol. 9. 1996. pp. 309–315.

Hermanson, Greg T. "Modification with Synthetic Polymers." *Bioconjugate Techniques*. Ch. 15. Academic Press, Inc.: San Diego, 1996. pp. 605–629.

Hoyle, Russ. "Genentech is poised for an anti–cancer breakthrough." Nature Biotechnology, Therapeutics Commentary. vol. 16. Oct. 1998. p. 887.

Jiang, Frank N.; Liu, Daniel J.; Neyndorff, Herma; Chester, Michael; Jiang, Shi–yi; and Levy, Julia G. "Photodynamic Killing of Human Squamous Cell Carcinoma Cells Using a Monoclonal Antibody–Photosensitizer Conjugate." Journal of the National Cancer Institute. vol. 83, No. 17. Sep. 4, 1991. pp. 1218–1225.

Khawli, L. A. and Epstein, A. L. "Exploration of novel strategies to enhance monoclonal antibodies targeting." The Quarterly Journal Of Nuclear Medicine. vol. 41, No. 1. 1997. pp. 25–35

Kostron, H.; Obwegeser, A.; and Zimmerman, A. "First clinical results of mTHPC–mediated PDT in malignant brain tumours." Abstract RC64. Dept. Neurosurg. and Physics, University Innsbruck. Undated. 1 pg.

Muller, PJ and Wilson, BC. "Photodynamic Therapy [PDT] For Brain Tumors." Abstract RC63. St. Michael's Hospital and the Princess Margaret Hospital, University of Toronto, Canada. Undated. 1 pg.

Torchilin, V. P. "Polymer–coated long–circulating microparticulate pharmaceuticals." J. Microencapsulation. Review, vol. 15, No. 1. 1998. pp. 1–19.

Westermann, Patrick; Glanzmann, Thomas; Andrejevic, Snezana; Braichotte, Daniel R.; Forrer, Martin; Wagnieres, Georges A.; Monnier, Philippe; Van Den Bergh, Hubert; Mach, Jean–Pierre; and Folli, Silvio. "Long Circulating Half–Life And High Tumor Selectively Of The Photosensitizer Meta–Tetrahydroxyphenylchlorin Conjugated To Polyethylene Glycol In Nude Mice Grafted With A Human Colon Carcinoma." Int. J. Cancer. vol. 76, 1998. pp. 842–850.

Zalipsky, Samuel. "Functionalized Poly(ethylene glycol) for Preparation of Biologically Relevant Conjugates." Bioconjugate Chem., Reviews. vol. 6. 1995. pp. 150–165.

\* cited by examiner

TUMOR WITH TARGETED POLYMER PROTECTED ANTIBODY/ PHOTOSENSITIZER CONJUGATES LINKED TO ABNORMAL TISSUE

FIG. 7

TUMOR WITH TARGETED POLYMER PROTECTED ANTIBODY/ PHOTOSENSITIZER CONJUGATES LINKED TO ABNORMAL TISSUE

USE OF PEGYLATED PHOTOSENSITIZER CONJUGATED WITH AN ANTIBODY FOR TREATING ABNORMAL TISSUE

FIELD OF THE INVENTION

The present invention is generally related to the use of light therapy to destroy abnormal tissue that has absorbed a photosensitizer, and more specifically, to the use of a photosensitizer that is targeted to bind with the abnormal tissue, but not normal tissue, so that the light administered during the therapy has a minimal adverse effect on surrounding normal tissue, which is generally free of the photosensitizer.

BACKGROUND OF THE INVENTION

Abnormal tissue in the body is known to selectively absorb certain photosensitizer dyes that have been administered to a patient to a much greater extent than normal tissue surrounding a treatment site. For example, tumors of the pancreas and colon may absorb two to three times the volume of these dyes, compared to normal tissue. The cancerous or abnormal tissue that has absorbed the photosensitizer dye can then be destroyed by administering light of an appropriate wavelength or waveband corresponding to an absorbing wavelength or waveband of the photosensitizer dye. This procedure, which is known as photodynamic therapy (PDT), has been clinically used to treat metastatic breast cancer, bladder cancer, lung carcinomas, esophageal cancer, basal cell carcinoma, malignant melanoma, ocular tumors, head and neck cancers, and other types of malignant tumors. Because PDT may selectively destroy abnormal tissue that has absorbed more of the dye than normal tissue, it can successfully be used to kill the malignant tissue of a tumor with less effect on surrounding benign tissue than alternative treatment procedures, such as traditional chemotherapy or radiation therapy.

However, even those photosensitizers that are much more selectively absorbed by abnormal tissue will still be absorbed to some lesser extent by the normal tissue of a patient's body. If the light therapy administered is limited primarily to the abnormal tissue at the treatment site so that very little light is applied to the adjacent normal tissue, which has absorbed the photosensitizer to a lesser extent, the effect of the light therapy on such normal tissue will be minimal. To enable the selective application of light therapy to an internal treatment site with minimal exposure of surrounding normal tissue, it is typically necessary to either surgically expose the internal treatment site, or insert an appropriate light source probe into the patient's body and advance it to the treatment site, for example, using conventional endoscopic procedures, or insert a light source probe interstitially into a tumor.

More recently, techniques have been developed for administering light therapy to an internal treatment site from an externally disposed light source. These techniques take advantage of the fact that light having a relatively long wavelength will readily penetrate dermal tissue to activate photosensitizers absorbed by abnormal tissue at an internal treatment site. The disadvantage of this approach is that normal tissue lying between the light source and the internal treatment site is also is irradiated by the light as it passes through the overlying tissue to the internal treatment site. Skin and other normal tissue in the propagation path of the light administered externally to render PDT to an internal treatment site will thus be adversely affected by the therapy. The effects of the light therapy on normal tissue that has absorbed the photosensitizer may range from mild reddening of the skin to severe damage to the normal dermal tissue. Clearly, it would be desirable to minimize damage to the normal tissue by substantially reducing the extent to which the normal skin and tissue absorb the photosensitizer.

One approach developed to address the preceding problems is to bind antibodies to a photosensitizer that are targeted to the abnormal cells at a treatment site. When a photosensitizer conjugated with an antibody is administered to a patient, the antibodies will tend to bind the photosensitizer to the abnormal tissue, but not to normal tissue, thereby improving the specificity of the PDT and avoiding harm to the normal tissue. However, it has been shown that targeted photosensitizers that are conjugated with an antibody can have a relatively low uptake by abnormal tissue in a tumor. In some cases, as little as 0.1% of an injected dose of photosensitizer is actually absorbed by the abnormal cells in a tumor. The low tumor uptake of antibody targeted photosensitizers (or other drugs) is due in part to the rapid plasma clearance by the reticuloendothelial system and poor penetration of the targeted conjugate across vascular endothelium. In effect, the targeted photosensitizer is cleared too rapidly from the plasma in the patient's body to have an opportunity to bind the antibody with the abnormal tissue at the levels desired.

More generally, too rapid clearance of conventional photosensitizers (i.e., a non-targeted photosensitizer) from plasma has also been recognized as problem. One solution that has been explored is the use of a synthetic drug carrier such as polyethylene glycol (PEG). As previously reported by others, PEG coated microparticulates containing a photosensitizer (zinc phthalocyanine) have been tested in vivo. In addition, V.P. Torchilin has published an article entitled, "Polymer-coated Long-Circulating Microparticulate Pharmaceuticals," in Journal Microencapsulation, vol. 15, no. 1, (1998) pp. 1–19, in which he discusses the protective effect of certain polymers, including PEG, on nanoparticulate drug carriers, including micelles, for extending the circulation time of the encapsulates in solution. PEG is well known as a sterically protecting polymer and drug carrier. Useful biological properties of PEG include its water solubility, low immunogenicity, and extended life while circulating in mammalian organisms. A PEG dextran conjugate has been used as a combined stabilizer and surface modifier to produce resorbable poly(DL-lactide-co-glycolide) (PLG) microparticles by an emulsification/solvent technique as described by A.G.A. Coombes et al. in "Biodegradable Polymeric Microparticles for Drug Delivery and Vaccine Formulation: the Surface Attachment of Hydrophilic Species Using the Concept of Poly(ethylene glycol) Anchoring Segments," in Biomaterials 1997, vol. 18, No. 17, page 1153. However, it appears that protectively polymerized drugs have not been conjugated with antibodies that can target the drugs to abnormal tissue. Clearly, the combination of a polymer such as PEG to protect a photosensitizer that is conjugated with an antibody could solve both the too rapid clearing of conventional targeted photosensitizer conjugates from the plasma and ensure that the photosensitizer binds only to the abnormal tissue, to substantially eliminate any damage to the normal tissue by the light therapy. Such a combination has not been disclosed or suggested by the prior art.

SUMMARY OF THE INVENTION

In accord with the present invention, a method for destroying abnormal tissue within a patient's body is defined. The method includes the step of providing a photosensitizer that is characterized by absorbing light within a defined waveband. The photosensitizer is sterically protected by a polymer and is conjugated with an antibody that is targeted at the abnormal tissue, producing a polymer protected antibody/photosensitizer conjugate. When the polymer protected antibody/photosensitizer conjugate is administered to the patient, the antibody portion of the conjugate preferentially links with the abnormal tissue at the treatment site, while the polymer increases an in vivo residence time of the antibody/photosensitizer conjugate within the patient's body. Consequently, there is an increased uptake of the antibody/photosensitizer conjugate by the abnormal tissue at the treatment site. Light within the defined waveband is administered to the internal treatment site, thereby activating the photosensitizer to destroy the abnormal tissue.

The polymer in the above-described method is preferably polyethylene glycol or a derivative of polyethylene glycol and is water soluble, hydrophilic, and biocompatible. In addition, the polymer exhibits a low toxicity and a low immunogenicity, is not biodegradable, and does not form any toxic metabolites. Other desired characteristics of the polymer include a high enough molecular weight, combined with a highly flexible main chain to provide for long in vivo residence times in a human body. The polymer should have at least one attachment site to which the photosensitizer and antibody may be covalently bonded.

The wavelengths of the light used when administering the light therapy from an external source are sufficiently long to readily pass through a dermal layer and through intervening tissue to reach the internal treatment site. Instead of being administered externally, the light may be administered internally using a light source disposed interstitially so that the light is administered to the treatment site within a patient's body.

The treatment site may be localized, such as at a tumor, or it may be disseminated throughout at least a portion of the patient's body, and the abnormal tissue may be distributed throughout the treatment site. The treatment site may include at least part of a vascular system of the patient in which the abnormal tissue is disposed. Furthermore, the abnormal tissue may be a tumor, non-localized malignant cells, or may be a disease causing bacteria or a disease causing virus.

The method described above may serve as a prophylaxis by administering the polymer protected antibody/photosensitize conjugate and administering light to a prospective treatment site at which abnormal tissue may possibly develop. This prophylactic treatment may be repeated at intervals to prevent development of the abnormal tissue within the patient.

It is also contemplated that the method described above may be used following the surgical removal of a substantial portion of the abnormal tissue, to destroy any residual abnormal tissue at the treatment site, or following the transplanting of bone marrow into a patient, to destroy residual abnormal tissue in the patient's body.

Another aspect of the present invention is directed to a method to improve a specificity with which a photosensitizer is taken up by abnormal cells within a patient. In this further aspect of the invention, a microparticle, a photosensitizer, an antibody that is targeted at antigens on the abnormal cells, and a polymer are provided. The antibody and the photosensitizer are conjugated to the microparticle, and the microparticle is coated with a polymer that prolongs an in vivo residence time for the microparticle based antibody/photosensitizer conjugate. When the polymer coated microparticle based antibody/photosensitizer conjugate is administered to a patient, the antibody on the conjugate links with the abnormal cells. The linking action of the antibody and ability of the polymer coating to increase the in vivo residence time results in a higher uptake of the polymer coated microparticle based antibody/photosensitizer conjugate by the abnormal cells than would be possible using a microparticle based antibody/photosensitizer conjugate that is not coated with the polymer.

The microparticle may comprise a micelle. Preferably, the polymer is PEG.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Polymer Protected Antibody/Photosensitizer Conjugates

Figure 1:
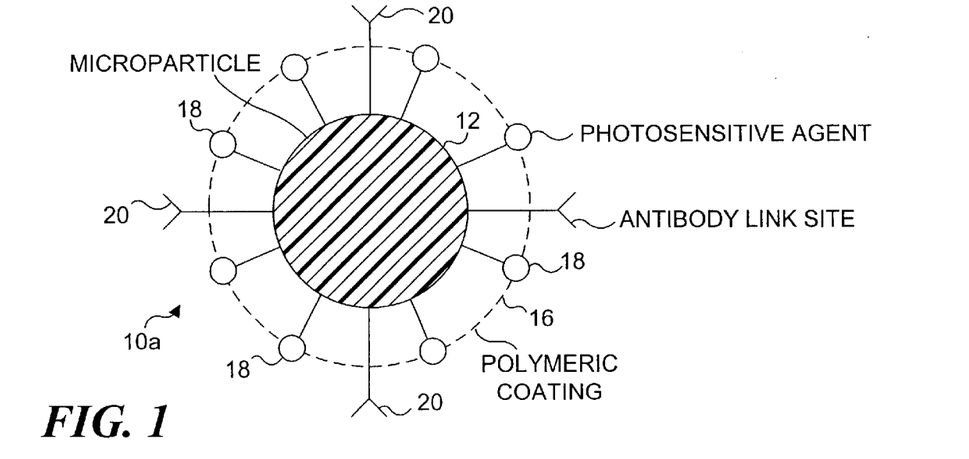
FIG. 1 schematically illustrates a first form of a polymer protected antibody/photosensitizer conjugate microparticle.

Referring to FIG. 1, a polymer protected antibody/photosensitizer conjugate 10a in accordance with the present invention is schematically illustrated. Polymer protected antibody/photosensitizer conjugate 10a includes a microparticle core 12 of the type normally used as a drug carrier. It is contemplated that the microparticle may be a micelle or a carrier, such as a latex sphere. Other inert, biocompatible microparticles may be used for the core or carrier. The choice of the particular microparticle will be determined by a number of factors, including the chemical compatibility of the microparticle with the antibody, the photosensitizer, and the polymer.

Attached to the surface of microparticle core 12 are a plurality of antibody linking sites 20, which are specifically targeted to link with antigens on abnormal tissue, or malignant cell organelles, or disease causing organisms within a patient's body. Note that as used herein and in the claims that follow, unless otherwise evident from the context, the term "abnormal tissue" is intended to encompass malignant cell organelles and disease causing organisms. Also attached to the surface of microparticle core 12 are a plurality of photosensitizers 18 of the type suitable for use in administering PDT.

Microparticle core 12 is coated with a polymer 16. Polymer 16 increases the in vivo residence time of the antibody/photosensitizer conjugates within the patient's body, e.g., within the plasma, allowing a lower dose of the photosensitizer conjugate to be used, while simultaneously increasing the uptake of the antibody/photosensitizer conjugate by the abnormal tissue. Polymer 16 is preferably polyethylene glycol (PEG) or PEG based, having a moderately high molecular weight, e.g., on the order of 20,000. Other polymers that exhibit similar properties may also be used to extend the residence time of the photosensitizer targeted conjugate within the patient's body. The polymer selected for this purpose must be: water soluble, hydrophilic, biocompatible, must exhibit a low toxicity, and must have a low immunogenicity. In addition, the polymer must not be biodegradable or form any toxic metabolites, must have a sufficiently high molecular weight, coupled with a highly flexible main chain, to provide for relatively long in vivo residence times in a human body, e.g., for more than several hours, and must be chemically compatible with the photosensitizer and antibody used for the conjugate.

An understanding of how the polymer coating results in longer in vivo residence times is helpful in designing a microparticle based polymer protected antibody/photosensitizer conjugate in accord with the present invention. Polymer 16 comprises a long, highly flexible main chain and has a moderately high molecular weight (which means that the main chain is longer in length than most molecules). The flexible main chain is in constant motion, creating a "cloud," which protects the surface of the microparticle and dramatically increases in vivo residence times. However, this same "cloud" may also tend to inhibit antibody link sites 20 from successfully binding with corresponding antigens on the target abnormal tissue. The prior art teaches that relatively minor amounts (1–2 mol%) of a polymer such as PEG provide sufficient protection to increase in vivo residence time, while higher concentrations tend to inhibit antibody linking. It is therefore anticipated that the optimal concentration of polymer used in producing a conjugate will need to be empirically determined for each different microparticle based polymer protected antibody/photosensitizer conjugate species.

Figure 2:
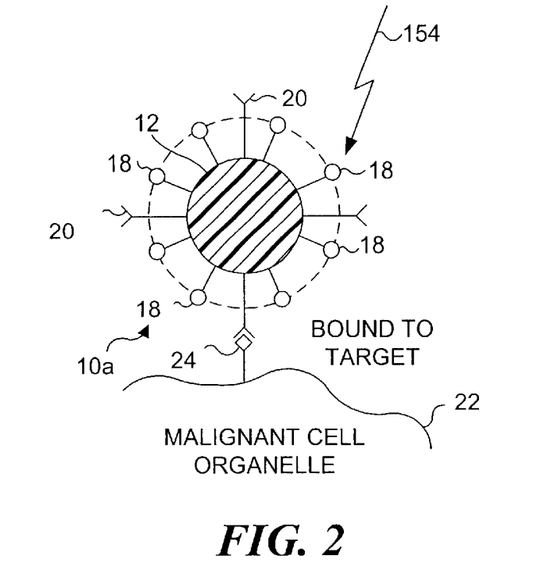
FIG. 2 is a schematic view showing the polymer protected antibody/photosensitizer conjugate of FIG. 1 bound to a target malignant cell organelle by the antibody.

FIG. 2 illustrates how targeted polymer protected antibody/photosensitizer conjugate 10a is used for destroying a malignant cell organelle 22. In this Figure, targeted polymer protected antibody/photosensitizer conjugate 10a is shown with one of the antibody link sites 20 linked to an antigen 24 that is associated with the malignant cell organelle. Because normal cells do not have any antigen to which antibody link sites 20 will bind, targeted polymer protected antibody/photosensitizer conjugates 10a do not become bound to normal cells. After providing sufficient time for the targeted polymer protected antibody/photosensitizer conjugates to bind to the malignant cell organelles or other types of abnormal tissue within a patient's body, a light 154 having a waveband corresponding to a characteristic light absorption waveband of the photosensitizer is applied using one of the techniques disclosed hereinbelow. This light activates a photosensitizer 18, causing it to form new chemical species, such as free oxygen radicals, which attack the target malignant cells or other abnormal tissue.

Figure 3A:
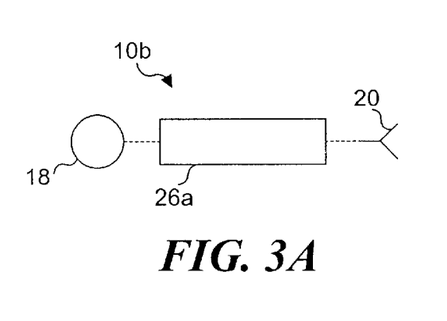
FIG. 3A schematically illustrates a second form of a polymer protected antibody/photosensitizer conjugate in which a photosensitizing agent and an antibody are bonded to a polymer at separate attachment sites.
Figure 3B:
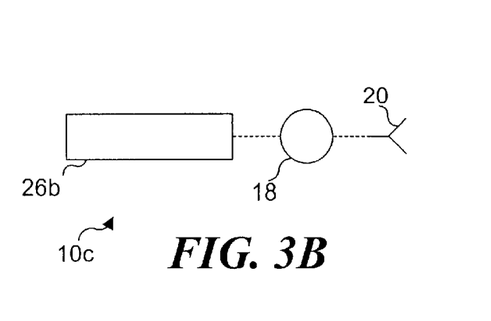
FIG. 3B schematically illustrates a third form of a polymer protected antibody/photosensitizer conjugate in which a photosensitizing agent and an antibody are bonded to a polymer at the same attachment site.

FIGS. 3A and 3B illustrate forms of polymer protected antibody/photosensitizer conjugates, which do not incorporate a microparticle core. In these embodiments, the antibody/photosensitizer conjugate is covalently bonded to the polymer rather than being attached to a microparticle. FIG. 3A illustrates polymer protected antibody/photosensitizer conjugate 10b in which photosensitizer 18 is covalently bonded to one attachment site of polymer 26a, while the antibody which includes antibody link site 20 is covalently bonded to a different attachment site of polymer 26a. Polymer 26a is preferably PEG, which has one attachment site at each end of the polymer chain.

FIG. 3B illustrates polymer protected antibody/photosensitizer conjugate 10c in which photosensitizer 18 is covalently bonded to one attachment site of polymer 26b, while the antibody which includes antibody link site 20 is covalently bonded to photosensitizer 18. Polymer 26b is preferably methyl-PEG, a PEG derivative which has only a single attachment site at one end of the polymer chain; the other attachment site having been replaced with a methyl group.

Figure 4:
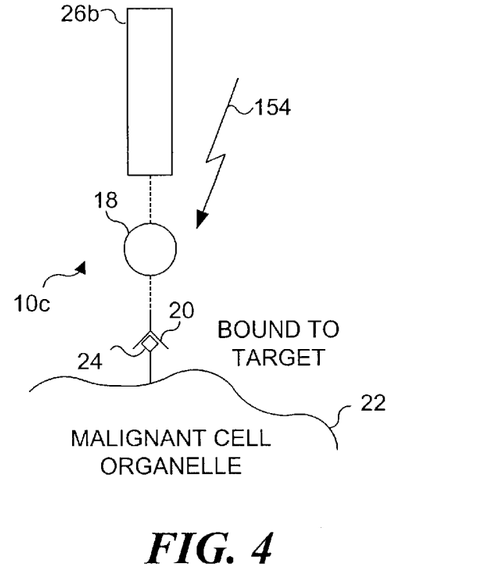
FIG. 4 is a schematic view of the third form of a polymer protected antibody/photosensitizer conjugate bound to a target malignant cell organelle by the antibody.

For the two forms of the polymer protected antibody/photosensitizer conjugate respectively illustrated in FIGS. 3A and 3B, it is important that antibody link site 20 be positioned in such a manner as to allow it easy access to corresponding antigen 24 on the targeted malignant cell organelle or other abnormal tissue, as illustrated in FIGS. 2 and 4. The relative positions of polymers 26a and 26b, antibody link site 20, and photosensitizer 18, as shown in FIGS. 3A and 3B, are not the only possible configurations. Actual positional configurations of the conjugates will be a function of the polymer chosen and the attachment sites available. Some polymers have a plurality of attachments sites available, thus a plurality of antibody link sites 20 and/or photosensitizers 18 may be covalently bonded to a single polymer molecule. The selection of polymer 26a or 26b will be based on the chemical compatibility of the polymer, antibody 20, and photosensitizer 18. Those skilled in the art will readily understand that appropriate chemical manipulations and processes will be required to form the desired polymer protected antibody/photosensitizer conjugate, and the ease or difficulty of such manipulations and processes will factor decisively in the ultimate configuration of the polymer protected antibody/photosensitizer conjugate employed.

FIG. 4 illustrates how targeted polymer protected antibody/photosensitizer conjugate 10c is used for destroying a malignant cell organelle 22. In a manner similar that of FIG. 2, targeted polymer protected antibody/photosensitizer conjugate 10c is shown with antibody link site 20 bound to an antigen 24. After providing sufficient time for targeted conjugates 10c to bind to the targeted abnormal tissue, light 154 of an appropriate waveband, i.e., corresponding to the absorption waveband of the photosensitizer, is applied using one of the techniques disclosed hereinbelow. The light activates photosensitizer 18, destroying the abnormal tissue.

Injection of Targeted Polymer Protected Antibody/Photosensitizer Conjugates

Figure 5:
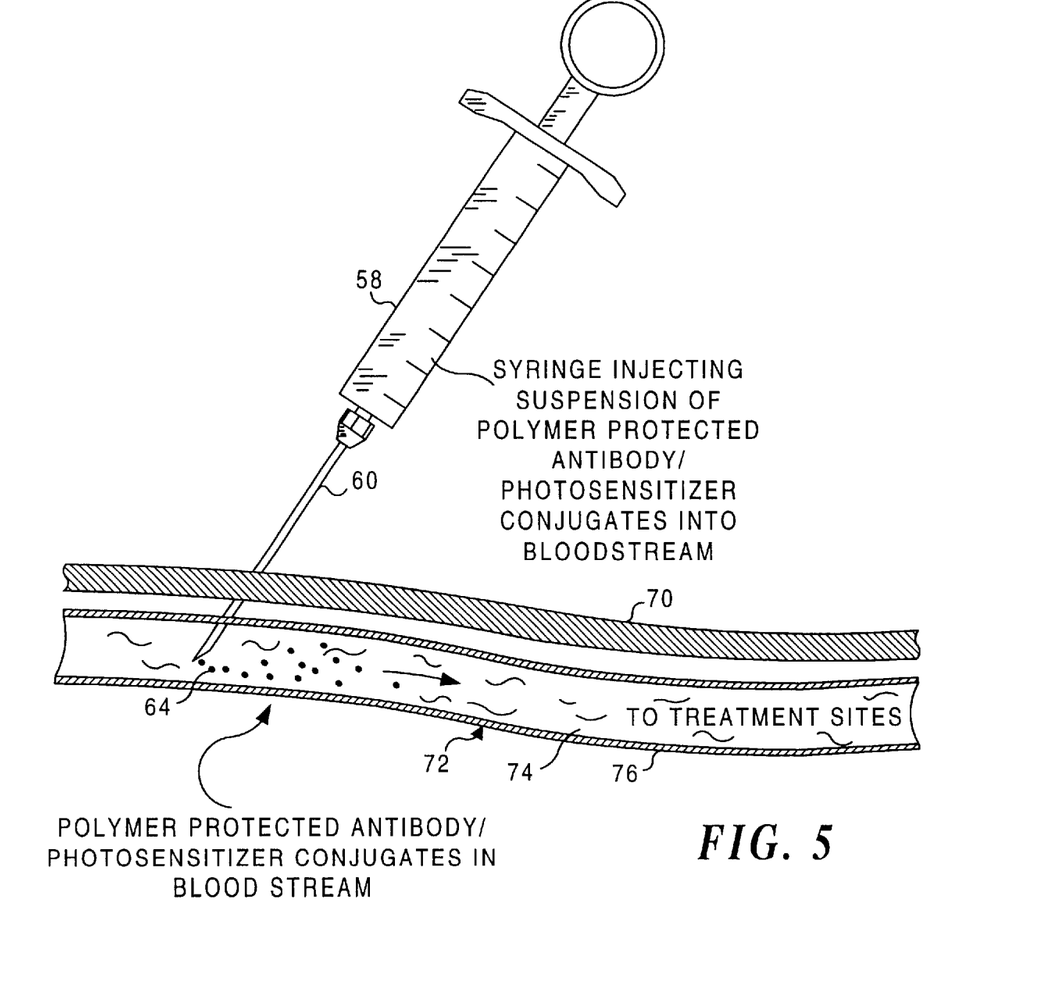
FIG. 5 is a schematic cross-sectional view of a portion of a patient's body in which a blood vessel is disposed, showing the polymer protected antibody/photosensitizer conjugates being injected into the patient's bloodstream with a syringe.

It is generally preferable to introduce the polymer protected antibody/photosensitizer conjugates as close as possible to a treatment site, such as by introducing the polymer protected antibody/photosensitizer conjugate directly into a tumor. At times, the location of a tumor or other treatment site is such that it is not feasible to localize the administration of the polymer protected antibody/photosensitizer conjugate. Furthermore, the targeted abnormal tissue may not be localized, but instead, may be viruses, microorganisms or metastasized cancer cells, which are more broadly distributed throughout a patient's body. It is therefore contemplated that polymer protected antibody/photosensitizer conjugates 10a, 10b, and 10c may be injected into the patient's bloodstream to allow the patient's own circulatory system to deliver the polymer protected antibody/photosensitizer conjugates to the targeted abnormal tissue. As illustrated in FIG. 5, a syringe 58 can be used to inject a fluid containing the targeted polymer protected antibody/photosensitizer conjugates in suspension through a dermal layer 70 and into a bloodstream 72. A needle 60 passes through dermal layer 70 and through a wall 76 of bloodstream 72; fluid containing the targeted polymer protected antibody/photosensitizer conjugates is injected through needle 60 into blood 74. The blood flow in the vessel carries the targeted polymer protected antibody/photosensitizer conjugates downstream, to one or more locations where the targeted abnormal tissue is disposed. It is important to note that antibody link sites 20 will seek out and bind only to the selected targeted abnormal tissue, which incorporates antigen 24, as shown in FIGS. 2 and 4. Since the photosensitizer is not linked to normal tissue, injury to normal tissue is minimized during administration of the light, particularly, if the light is administered from an external source and must pass through normal tissue to reach the abnormal tissue that has been targeted.

Activation of the Photosensitizer

The photosensitizer in the polymer protected antibody/photosensitizer conjugate destroys abnormal tissue to which it is bound when light of the proper waveband is administered. While the mechanism by which PDT destroys cells is not fully understood, it is believed to produce free oxygen radicals that are toxic to the abnormal tissue.

Figure 6:
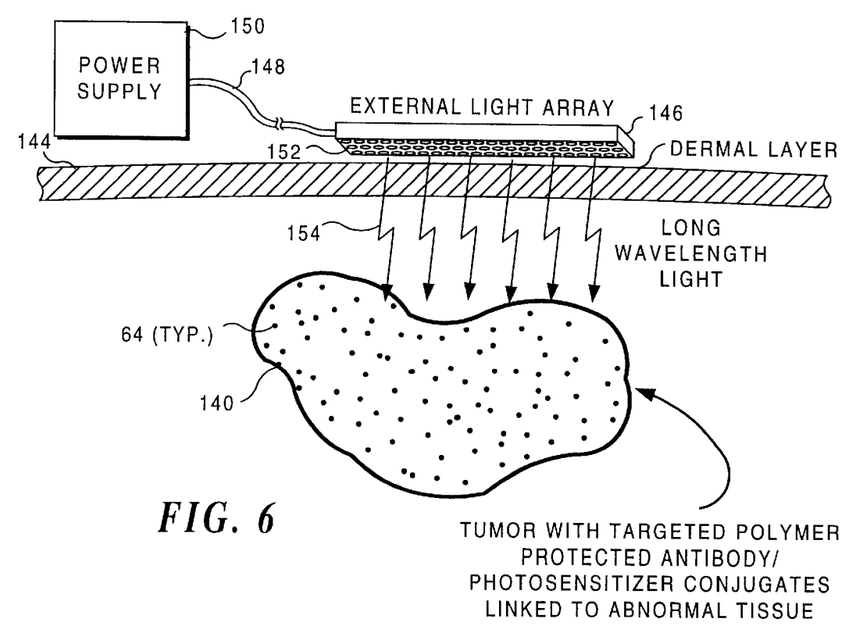
FIG. 6 is a schematic cross-sectional view of a portion of a patient's body containing a tumor, showing an external long wavelength light source being used to activate the photosensitizers in the polymer protected antibody/photosensitizer conjugates that are linked to the abnormal tissue in the tumor.

In FIG. 6, a tumor 140 has been infused with polymer protected antibody/photosensitizer conjugates 64. These conjugates may be of the forms illustrated in FIGS. 1, 3A, or 3B (i.e., conjugates 10a, 10b, and 10c, respectively). The polymer protected antibody/photosensitizer conjugates can be infused either within a biocompatible fluid, such as a physiological saline solution, or can be applied topically to the exterior surface of tumor 140. Tumor 140 lies within the patient's body, adjacent a dermal layer 144. Outside the patient's body, a power supply 150 is coupled through a lead 148 to an external light array 146. Array 146 comprises a plurality of light sources 152 such as LEDs. When energized by power supply 150, light sources 152 emit light 154 of the desired wavelength that passes freely through the dermal layer and into tumor 140, activating photosensitizer 18 that is included within polymer protected antibody/photosensitizer conjugates 64, so that photosensitizer 18 produces substances that attack tumor 140.

Figure 7:
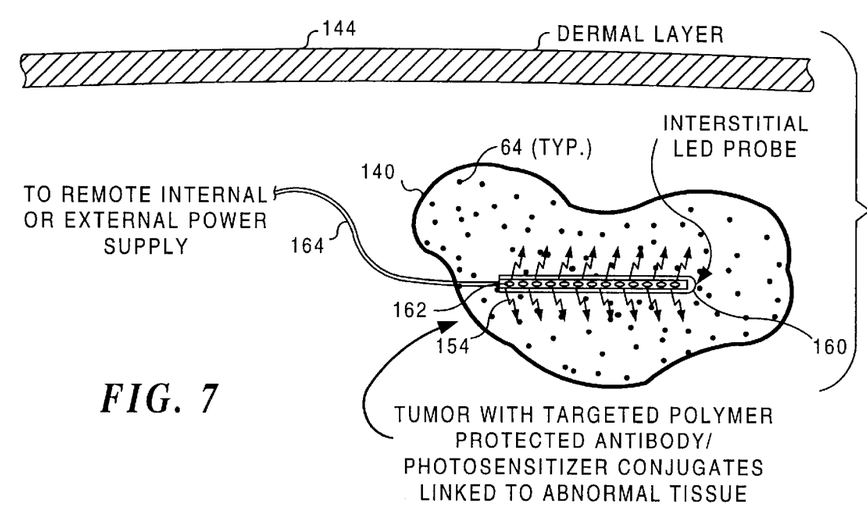
FIG. 7 is a schematic cross-sectional view of a portion of a patient's body containing a tumor, showing an internal light source being used to activate the photosensitizers in the polymer protected antibody/photosensitizer conjugates that are linked to the abnormal tissue in the tumor.

FIG. 7 illustrates yet another technique for exposing polymer protected antibody/photosensitizer conjugates 64 to light 154 of the waveband corresponding to the light absorption waveband of the photosensitizer. In this approach, a probe 160 is inserted interstitially within tumor 140. Probe 160 includes a linear array 162 of LEDs (or other appropriate light sources) that are energized through a lead 164. Lead 164 is coupled to a remote internal (or external) power supply (not shown). If disposed internally, the power supply can be energized using an external power source that is electromagnetically coupled to the internal power supply. A detailed description of apparatus suitable for providing such electromagnetic coupling is provided in U.S. Pat. No. 5,715, 837, which is assigned to the same assignee as the present invention, the disclosure and drawings of which are hereby specifically incorporated herein by reference.

As noted above, the targeted abnormal tissue may not be a localized tumor, but instead, may comprise metastasized cancer cells, disease causing viruses, disease causing bacteria or other undesirable microorganisms that are distributed throughout at least a portion of the patient's body. In this instance, the light employed for administering the light therapy preferably has a relatively long wavelength, e.g., longer than 800 nm, to enable the light to pass through several cm. of tissue. Generally, the longer the wavelength of the light, the greater its ability to penetrate tissue in the body of the patient. Of course, the light adsorption waveband of the photosensitizer must be matched to the wavelength or waveband of the light that is administered to activate the photosensitizer. It is contemplated that by passing a long wavelength light source over the external surfaces of a patient's body, the majority of the polymer protected antibody/photosensitizer conjugates attached to targeted abnormal tissue may be activated, thus destroying the abnormal tissue, even though widely disseminated within the patient's body.

It is also contemplated that polymer protected antibody/photosensitizer conjugates can be employed prophylactically to prevent the development of abnormal tissue at a prospective treatment site. For example, it is now possible to identify women with susceptibility to certain types of breast cancer based upon genetic testing. The probabilities of developing breast cancer in a women who has tested positive for the susceptible genes is so significant that some women choose to undergo prophylactic radical mastectomy to minimize the risk of later developing breast cancer. Instead, the present invention can provide an alternative prophylaxis, by providing for repetitive administration of a polymer protected antibody/photosensitizer conjugate targeted at the type of cancerous tumor cells that might develop, followed by administration of light therapy using light having a waveband corresponding to the light adsorption waveband of the photosensitizer. By periodically repeating such prophylactic therapy, development of cancerous tumor cells in the woman's breast can likely be prevented, but without the trauma involved in undergoing a radical mastectomy.

Another application of the present invention is for destroying any residual abnormal tissue that may remain at a tumor resection site, following surgical removal of the tumor. A common problem following such surgery is the regrowth of the tumor. After administering a polymer protected antibody/photosensitizer conjugate targeted at antibodies of the tumor that was removed, light therapy can be administered to destroy the residual tumor cells that have linked with the conjugate, thereby preventing the regrowth of the tumor. Such post-surgical treatment might be rendered, for example, following a mastectomy or brain tumor removal.

Yet another application of the present invention is in the treatment of leukemia or other diseases requiring bone marrow transplant. A polymer protected antibody/photosensitizer conjugate targeted at malignant antigens in the bone marrow can be administered followed by administration of light therapy using light of the appropriate waveband, as noted above. This treatment should be effective both pre- and post-bone marrow transplant to destroy much of the abnormal tissue causing the leukemia, and may be employed, in addition to more conventional radiation and chemotherapy treatments. It is also contemplated that the present invention may be used for destroying abnormal tissue in bone marrow, thereby avoiding the need for a bone marrow transplant. The polymer protected antibody/photosensitizer conjugate may be activated with light administered either from an interstitial source or an external source, i.e., transcutaneously or from within the patient's body.

While empirical evidence such as may be developed by clinical trials of the present invention have not yet been provided, it is believed by some authorities that antibodies like those used in the polymer protected antibody/photosensitizer conjugate may activate the body's own immune system. Furthermore, photodynamic activation of a photosensitizer has been demonstrated to also cause an immune response. It is expected that the present invention will produce a synergistic effect in enhancing the efficacy of PDT that is far greater than either of these processes alone. The use of a polymer such as PEG to protect a targeted photosensitizer is also expected to provide a much greater improvement in the efficacy of the conjugate than might be expected relative to the use of a PEG photosensitizer conjugate alone or a targeted photosensitizer alone.

Although the present invention has been described in connection with the preferred forms of practicing it and modifications thereto, those of ordinary skill in the art will understand that many other modifications can be made within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for destroying abnormal tissue in a patient, at an internal treatment site comprising the steps of:
    (a) providing a conjugate of a microparticle, a photosensitizer, an antibody and a polymer, the microparticle characterized by being inert and biocompatible, the photosensitizer characterized by absorbing light within a defined waveband, the polymer characterized by having a high molecular weight combined with a highly flexible main chain, thereby providing steric protection to the conjugate, and the antibody characterized by being targeted to an antigen which exists substantially only at the abnormal tissue in the patient;
    (b) administering the conjugate to the patient, said antibody linking with the abnormal tissue at the treatment site, and said polymer increasing an in vivo residence time of the conjugate to allow for an increased uptake of the conjugate by the abnormal tissue at the treatment site; and
    (c) administering light within the defined waveband to the internal treatment site, said light activating the photosensitizer to destroy the abnormal tissue.

2. The method of claim 1, wherein the polymer comprises polyethylene glycol.

3. The method of claim 1, wherein the polymer comprises a derivative of polyethylene glycol.

4. The method of claim 1, wherein the polymer is water soluble and hydrophilic.

5. The method of claim 1, wherein the polymer is biocompatible, exhibiting a low toxicity and a low immunogenicity in a concentration administered to the patient.

6. The method of claim 1, wherein the polymer must have at least one attachment site to which the photosensitizer and the antibody covalently bond.

7. The method of claim 1, wherein the defined waveband includes wavelengths sufficiently long to readily pass through a dermal layer of the patient.

8. The method of claim 7, wherein the light is administered externally to a body of the patient and passes through intervening tissue to reach the internal treatment site.

9. The method of claim 8, wherein the abnormal tissue is distributed throughout at least a portion of a body of the patient.

10. The method of claim 8, wherein the treatment site includes at least part of a vascular system of the patient, said abnormal tissue being disposed within said at least part of the vascular system.

11. The method of claim 1, wherein the abnormal tissue includes at least one of a disease causing bacteria and a disease causing virus.

12. The method of claim 1, wherein the step of administering the light includes the step of inserting a light source that emits light interstitially within the internal treatment site so that the light is administered to the internal treatment site.

13. The method of claim 1, wherein the internal treatment site is a prospective treatment site at which abnormal tissue may possibly develop, further comprising the steps of:
    (a) administering the conjugate to the patient; and
    (b) as a prophylaxis, administering the light to the prospective treatment site.

14. The method of claim 13, wherein the steps of administering the conjugate and administering the light as a prophylaxis are repeated at spaced-apart intervals of time to prevent development of the abnormal tissue at the prospective treatment site from occurring.

15. The method of claim 1, further comprising the step of surgically excising a substantial portion of the abnormal tissue, followed by the steps of administering the conjugate, and administering the light, to destroy any residual abnormal tissue at the treatment site.

16. The method of claim 1, further comprising the step of transplanting bone marrow into the patient, followed by the steps of administering the polymer protected antibody/photosensitizer conjugate, and administering the light, to destroy residual abnormal tissue in the patient.

17. A method for enhancing an efficacy of a light therapy rendered to destroy abnormal tissue, comprising the steps of:
    (a) administering a microparticle, polyethylene glycol (PEG), and a photosensitizer that is conjugated with an antibody targeted to bind with antigens present on the abnormal tissue, said polyethylene glycol serving to extend a viable lifetime of a resulting conjugate to enable more of said antibody to bind with the antigens on the abnormal tissue, thereby increasing an uptake of the conjugate by the abnormal tissue; and
    (b) after sufficient time has elapsed following administration of the conjugate to permit the antibody to bind with the antigens, administering a light therapy, said light therapy activating the photosensitizer and more effectively destroying the abnormal tissue due to the increased uptake of the conjugate by the abnormal tissue.

18. The method of claim 17, wherein the conjugated photosensitizer and antibody are coated with said PEG.

19. The method of claim 17, wherein conjugated photosensitizer and antibody is covalently bonded to said PEG.

20. The method of claim 17, wherein conjugated photosensitizer and antibody are covalently bonded to different sites on said PEG.

21. A method for preventing abnormal tissue growth in a patient, at a prospective treatment site at which abnormal tissue may possibly develop, comprising the steps of:
    (a) providing a conjugate comprising a photosensitizer, an antibody, and a polymer, the photosensitizer characterized by absorbing light within a defined waveband, the polymer characterized by having a high molecular weight combined with a highly flexible main chain, thereby providing steric protection to the conjugate, and the antibody characterized by being targeted to an antigen which exists substantially only at abnormal tissue in the patient;

(b) administering the conjugate to the patient, said antibody linking with any abnormal tissue at the prospective treatment site, and said polymer increasing an in vivo residence time of the conjugate to allow for an increased uptake of the conjugate by any abnormal tissue at the prospective treatment site; and (c) as a prophylaxis, administering light within the defined waveband to the prospective treatment site, said light activating the photosensitizer to destroy any abnormal tissue being formed.

22. The method of claim 21, wherein the steps of administering the conjugate and administering the light as a prophylaxis are repeated at spaced-apart intervals of time to prevent development of abnormal tissue at the prospective treatment site from occurring.

23. A method for destroying abnormal tissue in a patient, at a prospective treatment site at which a growth of the abnormal tissue may possible develop, comprising the steps of:

(a) providing a conjugate of a microparticle, a photosensitizer, an antibody and a polymer, the microparticle characterized by being inert and biocompatible, the photosensitizer characterized by absorbing light within a defined waveband, the polymer characterized by having a high molecular weight combined with a highly flexible main chain, thereby providing steric protection to the conjugate, and the antibody characterized by being targeted to an antigen which exists substantially only at abnormal tissue in the patient;

(b) administering the conjugate to the patient, said antibody linking with any abnormal tissue at the prospective treatment site, and said polymer increasing an in vivo residence time of the conjugate to allow for an increased uptake of the conjugate by any abnormal tissue at the prospective treatment site; and (c) as a prophylaxis, administering light within the defined waveband to the prospective treatment site, said light activating the photosensitizer to destroy abnormal tissue.

24. The method of claim 23, wherein the steps of administering the conjugate and administering the light as a prophylaxis are repeated at spaced-apart intervals of time to prevent development of abnormal tissue at the prospective treatment site from occurring.

25. A method for destroying abnormal tissue in a patient, at an internal treatment site, comprising the steps of:

(a) providing a polymer protected conjugate comprising a polymer suitable for increasing an in vivo residence time of said conjugate, a photosensitizer bound to said polymer, and a targeting antibody bound to said photosensitizer but not to said polymer, the photosensitizer being characterized by absorbing light within a defined waveband, the polymer being characterized by having a high molecular weight combined with a flexible main chain, thereby providing steric protection to the conjugate, and the antibody being characterized by being targeted to an antigen that exists substantially only at the abnormal tissue in the patient;

(b) administering the polymer protected conjugate to the patient, said antibody linking with the abnormal tissue at the treatment site, and said polymer increasing the in vivo residence time of the conjugate to provide sufficient time for uptake of the conjugate by the abnormal tissue at the treatment site; and (c) administering light within the defined waveband to the internal treatment site, said light activating the photosensitizer to destroy the abnormal tissue.

* * * * *